US00PP19869P2

(12) United States Plant Patent
Pierce

(10) Patent No.: US PP19,869 P2
(45) Date of Patent: Mar. 31, 2009

(54) ***CALIBRACHOA* PLANT NAMED 'CAL WHIROEN'**

(50) Latin Name: ***Calibrachoa* sp.**
Varietal Denomination: Cal Whiroen

(75) Inventor: Robert Pierce, Watsonville, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 12/080,148

(22) Filed: Mar. 31, 2008

(51) Int. Cl.
*A01H 5/00* (2006.01)

(52) U.S. Cl. ..... Plt./413
(58) Field of Classification Search ..... Plt./413
See application file for complete search history.

*Primary Examiner*—Annette H Para
(74) *Attorney, Agent, or Firm*—C. A. Whealy

(57) ABSTRACT

A new and distinct cultivar of *Calibrachoa* plant named 'Cal Whiroen', characterized by its mounding and outwardly spreading to trailing plant habit; freely branching habit; dense and full plants; early and freely flowering habit; numerous white-colored flowers with red purple-colored centers and venation; and good garden performance.

1 Drawing Sheet

Botanical designation: *Calibrachoa* sp.
Cultivar denomination: 'Cal Whiroen'.

BACKGROUND OF THE INVENTION

The present invention relates to a new and distinct cultivar of *Calibrachoa,* botanically known as *Calibrachoa* sp. and hereinafter referred to by the name 'Cal Whiroen'.

The new *Calibrachoa* is a product of a planned breeding program conducted by the Inventor in Gilroy, Calif. The objective of the breeding program is to create new *Calibrachoa* cultivars with uniform plant habit and numerous attractive flowers.

The new *Calibrachoa* originated from a cross-pollination made by the Inventor in July, 2004 in Gilroy, Calif. of a proprietary selection of *Calibrachoa* sp. identified as code number 966-1, not patented, as the female, or seed, parent with a proprietary selection of *Calibrachoa* sp. identified as code number 917-1, not patented, as the male, or pollen, parent. The new *Calibrachoa* was discovered and selected by the Inventor as a single flowering plant within the progeny of the stated cross-pollination in a controlled environment in Gilroy, Calif. in September, 2005.

Asexual reproduction of the new *Calibrachoa* by vegetative cuttings in a controlled environment in Gilroy, Calif. since September, 2005 has shown that the unique features of this new *Calibrachoa* are stable and reproduced true to type in successive generations.

SUMMARY OF THE INVENTION

The cultivar Cal Whiroen has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Cal Whiroen'. These characteristics in combination distinguish 'Cal Whiroen' as a new and distinct cultivar of *Calibrachoa:*

1. Mounding and outwardly spreading to trailing plant habit.
2. Freely branching habit; dense and full plants.

3. Early and freely flowering habit.
4. Numerous white-colored flowers with red purple-colored centers and venation.
5. Good garden performance.

The new *Calibrachoa* can be compared to plants of the female parent selection. Plants of the new *Calibrachoa* differ from plants of the female parent selection in the following characteristics:

1. Plants of the new *Calibrachoa* have darker green-colored leaves than plants of the female parent selection.
2. Plants of the new *Calibrachoa* have larger flowers than plants of the female parent selection.
3. Plants of the new *Calibrachoa* and the female parent selection differ in flower color as plants of the female parent selection have light purple-colored flowers with purple-colored venation.

Plants of the new *Calibrachoa* can be compared to plants of the male parent selection. Plants of the new *Calibrachoa* differ from plants of the male parent selection in the following characteristics:

1. Plants of the new *Calibrachoa* are more prostrate than plants of the male parent selection.
2. Plants of the new *Calibrachoa* flower earlier than plants of the male parent selection.
3. Plants of the new *Calibrachoa* have larger flowers than plants of the male parent selection.

Plants of the new *Calibrachoa* can be compared to plants of the cultivar Kakegawa S9, not patented. In side-by-side comparisons conducted in Hillscheid, Germany, plants of the new *Calibrachoa* differed from plants of the cultivar Kakegawa S9 in the following characteristics:

1. Plants of the new *Calibrachoa* were more freely branching than plants of the cultivar Kakegawa S9.
2. Plants of the new *Calibrachoa* flowered earlier than plants of the cultivar Kakegawa S9.
3. Plants of the new *Calibrachoa* were more freely flowering than plants of the cultivar Kakegawa S9.

BRIEF DESCRIPTION OF THE PHOTOGRAPH

The accompanying colored photograph illustrates the overall appearance of the new *Calibrachoa*, showing the colors as true as it is reasonably possible to obtain in colored reproductions of this type. Colors in the photograph may differ slightly from the color values cited in the detailed botanical description which accurately describe the colors of the new *Calibrachoa*. The photograph comprises a close-up view of a typical flowering plant of 'Cal Whiroen'.

DETAILED BOTANICAL DESCRIPTION

The aforementioned photograph and following observations, measurements and values describe plants grown in Hillscheid, Germany under commercial practice during the summer in an outdoor nursery. Plants used for the photograph were grown in 15-cm containers for about 16 weeks. Plants used for the description were grown in 25-cm hanging basket containers for about seven months. In the following description, color references are made to The Royal Horticultural Society Colour Chart, 2001 Edition, except where general terms of ordinary dictionary significance are used.

Botanical classification: *Calibrachoa* sp. cultivar Cal Whiroen.

Parentage:

*Female, or seed, parent.*—Proprietary selection of *Calibrachoa* sp. identified as code number 966-1, not patented.

*Male, or pollen, parent.*—Proprietary selection of *Calibrachoa* sp. identified as code number 917-1, not patented.

Propagation:

*Type.*—By vegetative cuttings.

*Time to initiate and develop roots.*—About 18 to 23 days.

*Root description.*—Fibrous; color, close to 155D.

Plant description:

*Plant and growth habit.*—Mounding and outwardly spreading to trailing plant habit. Freely branching habit with about seven to eight primary lateral branches each with about ten to twelve secondary lateral branches; full and dense plants. Vigorous growth habit.

*Plant height.*—About 21 cm to 23 cm.

*Plant diameter.*—About 55 cm.

Lateral branch description:

*Length.*—About 25 cm to 30 cm.

*Diameter.*—About 3 mm.

*Internode length.*—About 5 mm to 10 mm.

*Strength.*—Strong; flexible.

*Aspect.*—Initially upright to outwardly spreading to trailing.

*Texture.*—Densely hirsute.

*Color.*—Close to 146B, slightly tinted with 148A.

Foliage description:

*Arrangement.*—Alternate, simple.

*Length.*—About 2.5 cm to 3 cm.

*Width.*—About 1 cm to 1.3 cm.

*Shape.*—Elliptic.

*Apex.*—Obtuse.

*Base.*—Attenuate to acute.

*Margin.*—Entire.

*Texture, upper surface.*—Hirsute.

*Texture, lower surface.*—Hirsute; more dense at the margins and midrib.

*Venation pattern.*—Pinnate; arcuate.

*Color.*—Developing foliage, upper surface: Close to 137D. Developing foliage, lower surface: Close to 138A to 138B. Fully expanded foliage, upper surface: Close to 137C; venation, similar to lamina. Fully expanded foliage, lower surface: Close to 138A; venation, close to 145B.

*Petioles.*—Length: About 1 mm to 4 mm. Diameter: About 1 mm to 2 mm. Texture, upper and lower surfaces: Hirsute; more dense at the margins and midrib. Color, upper and lower surfaces: Close to 145B.

Flower description:

*Flower arrangement and habit.*—Single salverform flowers arranged singly arising from upper leaf axils. Freely flowering habit with usually about 40 flowers developing per plant. Flowers not persistent. Flowers face upright or outwardly.

*Fragrance.*—None detected.

*Natural flowering season.*—Plants of the new *Calibrachoa* initiate and develop flowers about eight weeks after planting. Plants flower continuously during the summer in Hillscheid, Germany.

*Flower longevity.*—Individual flowers last about five to eight days on the plant.

*Flower diameter.*—About 3 cm to 3.3 cm.

*Flower length (height).*—About 2.9 cm to 3.2 cm.

*Corolla tube length.*—About 1.7 cm to 1.9 cm.

*Flower bud.*—Shape: Oblong, elongate. Length: About 1.9 cm to 2 cm. Diameter: About 5 mm to 8 mm. Color: Close to 151B to 151C; towards the apex, close to 1D.

*Corolla.*—Arrangement: Five petals fused at the base and opening into a flared trumpet; flowers star-shaped. Petal shape: Roughly obovate. Petal apex: Slightly retuse. Petal margin: Entire; moderately undulate. Petal texture, upper and lower surfaces: Papillose, satiny; along the veins, hirsute. Color: Petal, when opening, upper surface: Close to 155A. Petal, when opening, lower surface: Close to 155C. Petal, fully opened, upper surface: Close to 155D; towards the throat and venation, close to either 59A to 59B or 60C. Petal, fully opened, lower surface: Close to 155C; venation, close to 145B. Throat: Close to 6B. Tube: Close to 4B.

*Calyx.*—Arrangement: One star-shaped calyx tube with five sepals fused at the base per flower. Sepal length: About 1.5 cm to 1.6 cm. Sepal width: About 3 mm to 4 mm. Sepal shape: Lanceolate. Sepal apex: Acute to obtuse. Sepal margin: Entire. Sepal texture, upper and lower surfaces: Densely hirsute; more dense on the lower surface and margins. Color, upper surface: Close to 137C to 137D. Color, lower surface: Close to 137C to 137D.

*Peduncles.*—Length: About 1.7 cm to 2.7 cm. Diameter: About 1 mm. Strength: Moderately strong; flexible. Texture: Densely hirsute. Color: Close to between 143C and 144B.

*Reproductive organs.*—Stamens: Quantity/arrangement: About five per flower. Filament length: About 8 mm to 11 mm. Filament diameter: About 1 mm. Filament color: Close to 154D. Anther shape: Reniform, two-parted. Pollen amount: Moderate. Pollen color: Close to 8A. Pistils: Quantity: One per flower. Pistil length: About 9 mm to 10 mm. Style color: Close to 145D. Stigma shape: Ovate. Stigma color: Close to 143C. Ovary color: Close to 145D. Seeds/fruits: Seed and fruit development have not been observed.

Garden performance: Plants of the new *Calibrachoa* have been observed to have good garden performance and tolerate wind, rain and temperatures ranging from about 5° C. to about 30° C.

Pathogen/pest resistance: Plants of the new *Calibrachoa* have not been observed to be resistant to pathogens and pests common to *Calibrachoa*.

It is claimed:

1. A new and distinct *Calibrachoa* plant named 'Cal Whiroen' as illustrated and described.

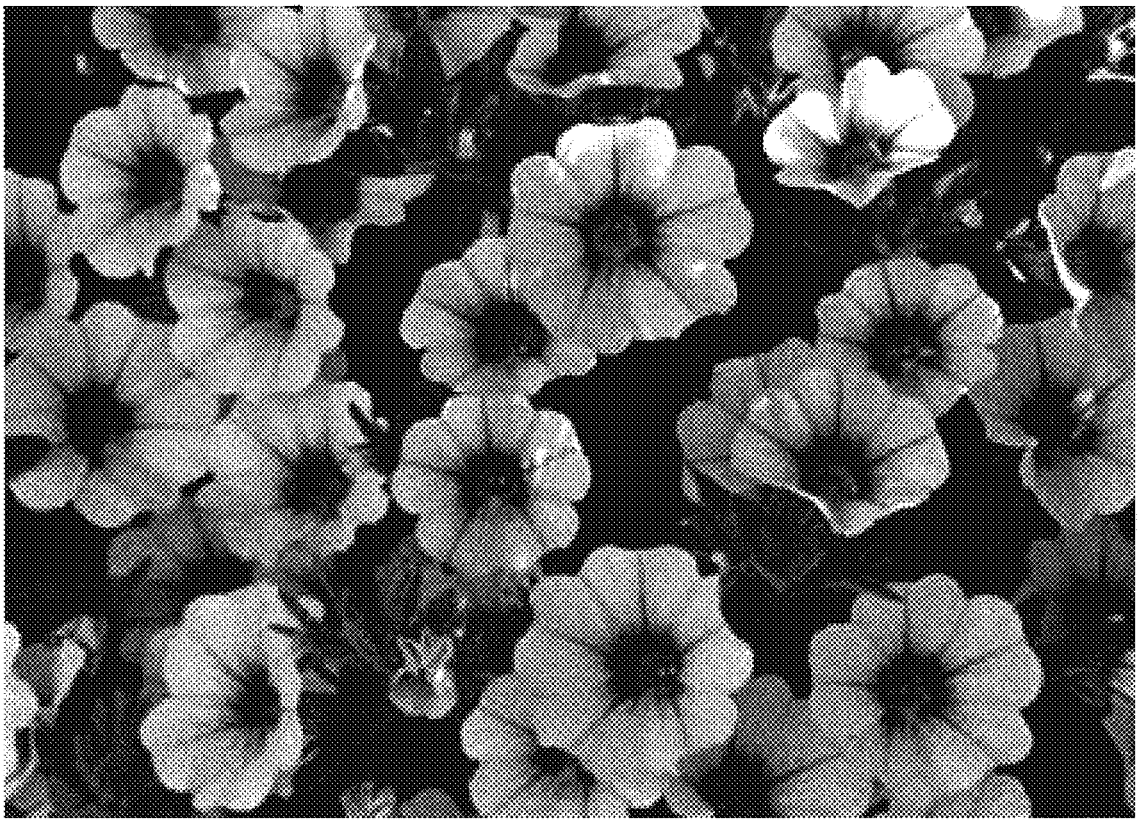

* * * * *